United States Patent [19]

Fiechtner et al.

[11] Patent Number: 4,970,074

[45] Date of Patent: Nov. 13, 1990

[54] FLUOROPHORES FOR ENCAPSULATION INTO LIPOSOMES

[75] Inventors: Michael D. Fiechtner; Christopher Bieniarz, both of Highland Park; Mohamed Shipchandler, Libertyville; Maciej Adamczyk, Lindenhurst, all of Ill.

[73] Assignee: Abbott Laboratories, Abbott Park, Ill.

[21] Appl. No.: 367,151

[22] Filed: Jul. 24, 1989

Related U.S. Application Data

[62] Division of Ser. No. 67,833, Jun. 29, 1987, Pat. No. 4,912,208.

[51] Int. Cl.$^5$ .................. C07D 311/82; C07D 473/08; A61K 43/00
[52] U.S. Cl. ..................................... 424/450; 536/53; 424/7.1; 424/9; 544/300; 549/223; 549/403; 558/8
[58] Field of Search ............................ 424/450, 7.1, 9; 536/53; 558/8; 549/223, 403; 544/300

[56] References Cited

U.S. PATENT DOCUMENTS

| | | | |
|---|---|---|---|
| 4,130,634 | 12/1978 | Molinaro et al. | 424/9 |
| 4,304,720 | 12/1981 | Dean et al. | 436/800 |
| 4,318,846 | 3/1982 | Khanna et al. | 530/806 |
| 4,342,826 | 8/1982 | Cole | 435/7 |
| 4,350,676 | 9/1982 | Laties et al. | 424/9 |
| 4,476,229 | 10/1984 | Fino et al. | 436/500 |
| 4,510,251 | 4/1985 | Kirkemo et al. | 436/501 |
| 4,614,823 | 9/1986 | Kirkemo et al. | 544/300 |
| 4,668,640 | 5/1987 | Wang et al. | 436/528 |

FOREIGN PATENT DOCUMENTS 10110186 11/1983 European Pat. Off. .
2069133 8/1981 United Kingdom .

OTHER PUBLICATIONS

Allen et al., Biochimica et Biophysica Acta., 597:4518–426 (1980).
Ishimiro et al., Journal of Immunological Methods, 75:351–360 (1984).
Kataoka et al., Eur. J. Biochem., 24:123–127 (1971).
Kendall et al., Analytical Biochemistry, 134:26–33 (1983).
Kendall et al., The Journal of Biological Chemistry, 257:13892–13895 (1982).
Lelkes et al., Biochimica et Biophysica Acta., 7616:410–419 (1982).
O'Connell et al., Clin. Chem., 31:1424–1426 (1985).
Struck et al., Biochemistry, 20:4093–4099 (1981).
Vanderwerf et al., Biochimica et Biophysica Acta., 596:302–314 (1980).
Weinstein et al., Science, 195:489–492 (1977).
Wilschut et al., Biochemistry, 19:6011–6021 (1980).
Yasuda et al., Journal of Immunological Methods, 44:153–158 (1981).
Haga et al., Analytical Biochemistry, 118:286–293 (1981).
Haga et al., Biochemical and Biophysical Research Communications, 95:187–192 (1980).
Gregoriadis et al., Biochem. J., 129–133 (1972).
Gregoriadis et al., Biochem., 24:485–491 (1972).
Hsia et al., Annals New York Academy of Sciences, 139–149(1978).
Uemura et al., Biochemistry, 11:4085–4094 (1972).
Six et al., Biochemistry, 12:4003–4011 (1973).
Six et al., Biochemistry, 13:4050–4058 (1971).
Ryman et al., Essays in Biochemistry, 16:49–98 (1980).
Wei et al., Journal of Immunological Methods, 9:165–170 (1975).
Smolarsky et al., Journal of Immunological Methods, 15:255–265 (1977).
Gregoriadis et al.,Nature, 244:170–172 (1973).
Sessa et al., J. of Biological Chemistry, 245:3295–3301 (1970).
Chan et al., J. of Immunological Methods, 21:185–195 (1978).
Haga, et al., Analytical Biochemistry, 118:286–293 (1981).
J. Barbet, "Traceurs Fluorescents Des Liposomes," Inserm. vol. 107, pp. 25–37.
Abbott Laboratories, "Substituted Carboxyfluoresceinc for Drug Determination in Body Fluids by Fluorescence Immunoassay," 107(23):50 abstract no. 211866c, Dec. 7, 1987.
Abbott Laboratories, "Aminophenol Derivatives for Immuno Chemical Analysis of Acetaminophen," 106(21): 70 abstract No. 169030c, May 25, 1987.

*Primary Examiner*—Ronald W. Griffin
*Attorney, Agent, or Firm*—Roberta L. Hastreiter

[57] ABSTRACT

The present invention provides novel fluorescein derivative compounds having fluorescence spectrum and quantum yield characteristics similar to those of fluorescein. The compounds are readily synthesized and purified and are readily soluble in water at self-quenching concentrations. Significantly, due to the presence of polar polyhydroxy group substituents and the absence of metal-chelating groups, these fluorescein derivatives are susceptible to minimal leakage across liposome membranes and have fluorescence characteristics minimally sensitive to the presence of metal ions. Compounds of the invention are thus exceptionally suitable for use in the development of highly storage stable liposome preparations to be employed in immunolytic assays involving human body fluid samples.

1 Claim, No Drawings

FLUOROPHORES FOR ENCAPSULATION INTO LIPOSOMES

This is a division of Ser. No. 067,833 filed June 29, 2987, now U.S. Pat. No. 4,912,208.

BACKGROUND OF THE INVENTION

The present invention relates to novel fluorescein derivatives, to liposome preparations involving the same and to immunoassay systems based on the use of such liposomes.

Liposomes are micron-sized spherical shells of amphipathic molecules which isolate an interior aqueous space from the bulk exterior aqueous environment. They can be made to contain hydrophobic molecules within their membrane, or hydrophilic markers within their internal aqueous space, or both. This versatility makes liposomes of interest both as potential vehicles for the delivery of drugs in vivo and as the basis for homogeneous immunoassay systems in vitro.

Several immunoassay systems utilizing liposomes have been described. For example, O'Connell, et al., *Clin. Chem.*, 31:1424–1426 (1985) describe a simple competitive binding immunoassay for detecting digoxin using liposomes encapsulating Sulforhodamine B as tracers. Another immunoassay system is the sensitive, homogeneous Liposome Immuno-Lytic Assay (LILA) which involves the antibody-triggered complement-mediated lysis of liposomes. In an exemplary assay format, a liposome encapsulating a marker is made immunoreactive by coupling, e.g., an antigen to the liposome surface, and is incubated with a fluid sample to be analyzed for the presence of antibodies immunoreactive with the antigen. The subsequent binding of a specific antibody to that antigen forms a liposome immune complex. Upon the addition of serum to this liposome complex, complement activation is initiated leading to lysis of the liposome and release of the internal marker substance.

Detection of this lytic event can be achieved in a variety of ways depending upon the nature of the marker initially encapsulated within the liposome. For example, Kataoka, et al., *Eur. J. Biochem.*, 24:123 (1971) describe sensitized liposomes which release trapped glucose marker when incubated with an appropriate anti-serum and complement source.

Numerous fluorescent markers have been successfully associated with or encapsulated within liposomes including both lipid-soluble compounds such as 1,6-diphenyl hexatriene, diacyl oxacarbocyanine, diacyl indocarbocyanine and 4-nitrobenzene 2-oxadiazole; and water-soluble compounds such as carboxyfluorescein, lucifer yellow, aminonapthalene trisulfonate and anilino-napthalene sulfonate, Barbet, J., *Fluorescent Tracers for Liposomes. Inserm*, 107: 27–36 (1982).

Various methods for the fluorescent detection of liposome lysis have been described including the encapsulation of a fluorophore at self-quenching concentrations followed by lysis and re-establishment of fluorescence, Weinstein, et al., *Science*, 195:489–491 (1977); dilution of a fluorophore and quencher Vanderwerf, et al., *Biochem. Biophys. Acta.*, 596:302–314 (1980), fluorescent complex formation, Wilschut, et al., *Biochemistry*, 19:6011–6021 (1980); quenching by complex formation, Kendall, et al., *J. Biol. Chem.*, 257:13892-5 (1982); and resonance energy transfer using two fluorophores, Struck, et al., *Biochemistry*, 20:4093–4099 (1981).

Where a fluorescent compound is encapsulated at self-quenching concentrations within the interior aqueous space of the liposome, upon liposome lysis an extreme dilution of the fluorophore occurs. A self-quenching concentration is defined to be that concentration at which the fluorescence of the fluorophore has been reduced relative to the fluorescence maximally attainable under conditions of extreme dilution. Subsequent dilution re-establishes fluorescence and the increase in fluorescence over background levels is, ideally, proportional to the concentration of the analyte present in the assay sample.

As one example, Ishimori, et al., *J. Immuno. Methods*, 75:351–360 (1984) describe an immunoassay technique using immunolysis of liposomes to measure antibody against protein antigens such as human IgG. The release marker used is carboxyfluorescein and the technique is assertedly effective at detecting $10^{-15}$ mole of anti-human IgG antibody, or, in an inhibition assay, human IgG. Yasuda et al., *J. Immun. Methods*, 44:153–158 (1981), describe the utilization of complement-mediated immune lysis of fluorescent dye encapsulating liposomes to measure anti-glycolipid antibody. Multilamellar liposomes containing carboxyfluorescein, self-quenched at high concentrations, are prepared and upon addition of anti-glycolipid serum plus active complement, liposome lysis occurs and trapped carboxyfluorescein is released.

The fluorophores most commonly used in liposome studies, fluorescein, carboxyfluorescein, and calcein, all show appreciable leakage over a short time scale of hours to days. Weinstein, et al., *Science*, 195:489–492 (1977), studying liposome-cell interactions, report that the half-time of fluorescein leakage at 5° C. is about 5 minutes whereas that of 6-carboxyfluorescein, a more polar derivative of fluorescein, is on the order of weeks.

Although carboxyfluorescein is less permeable than fluorescein across liposome membranes, the fluorescent yield of carboxyfluorescein is highly dependent upon pH and only the tri-anionic form has maximal fluorescence. The ionic strength, calcium concentration, and temperature of the solution have an influence on fluorescence. Moreover, Lelkes, P. et al., *Biochim. et Biophys. Acta.*, 716:410–419 (1982), investigating the stability of small unilamellar liposomes in human blood, report the need to correct for detergent and centrifugation effects as well as for passive liposome-blood cell association. The use of certain detergents resulted in strong fluorescence quenching and centrifugation of liposomes resulted in a 7–8.8% release of carboxyfluorescein from the liposomes. The addition of approximately 50 mol% cholesterol was required to significantly increase liposome stability. While carboxyfluorescein is highly fluorescent and has a lower leakage rate, fluorescent compounds that are more polar or more strongly ionic are often preferred because of their insensitivity to pH changes. Insensitivity to changes in pH is particularly advantageous because in those assay systems requiring complement lysis of liposomes, the pH may be readily adjusted for optimum complement activity and optimum assay sensitivity without affecting fluorophore leakage or signal.

The fluorescence of calcein, a more electronegatively charged derivative of fluorescein, is largely pH-independent over the pH range of 6.0–8.5. Leakage of calcein from a variety of phospholipid vesicles, as a function of temperature, and in the presence and absence of human serum is reported in Allen, T.M. et al.,

*Biochim. et Biophys. Acta.*, 597:418–426 (1980). The presence of serum signifanctly increased liposome leakage and the incorporation of increasing molar ratios of cholesterol into liposomes was required to reduce leakage of calcein from liposomes incubated with buffer and with serum. Leakage was significantly higher from liposomes with an osmotic gradient across the membrane (higher inside) than from equiosmolar liposomes.

Calcein can be an acceptable fluorophore in terms of leakage for those applications where the experiments are run the same day. However, it is frequently unacceptable for other applications due to its finite leakage and its susceptibility to quenching by metal ions, i.e., the chelating groups on the xanthene ring bind a large number of different metal ions, Kendall, et al., *Analytical Biochemistry*, 134:26–33 (1983). Calcein fluorescence is quenched by the binding of $Fe^{2+}$, $Fe^{3+}$, $Ni^{3+}$, $Mn^{2+}$, $Co^{2+}$ and $Tb^{3+}$. These metals can be common contaminants in water and in laboratory glassware. Since lysis in a liposome immunoassay is detected by the release of liposome contents and resultant increase in fluorescence, any quenching of fluorescence leads to an inaccurate measure of lysis and consequently an inaccurate assay result.

There continues to exist a need in the art for fluorescent compounds suitable for use in the preparation of fluorophore-encapsulated liposomes for lytic assays, including immunolytic assays, involving release of fluorophores maintained at self-quenching concentrations within the liposomes. Compounds of this type would be chemically stable and readily synthesized and purified. Ideally they would have a fluorescence spectrum similar to that of fluorescein (allowing use of existing fluorescence detection apparatus based on fluorescein spectral characteristics) and would provide quantum yields at around neutral pH which are no less than about 80% based on maximal fluorescein fluorescence. The compounds should have solubility characteristics allowing for encapsulation at self-quenching concentrations, yet have few ionizable groups in order to minimize osmotic effects. When projected for use in analytical systems wherein metal ions comprise part of the sample milieu, the fluorescence characteristics of the compounds should be minimally sensitive to such ions. The compounds should be susceptible to minimal leakage across liposome membrane layer(s).

BRIEF SUMMARY

The present invention provides novel fluorescein derivative compounds having fluorescence spectrum and quantum yield characteristics similar to those of fluorescein. The compounds are readily synthesized and purified and are readily soluble in water at self-quenching concentrations. Significantly, due to the presence of polar polyhydroxy group substituents and the absence of metal-chelating groups, these fluorescein derivatives are susceptible to minimal leakage across liposome membranes and have fluorescence characteristics minimally sensitive to the presence of metal ions. Compounds of the invention are thus exceptionally suitable for use in the development of highly stable liposome preparations to be employed in immunolytic assays involving human body fluid samples.

Presently preferred compounds of the invention are those of Formula I,

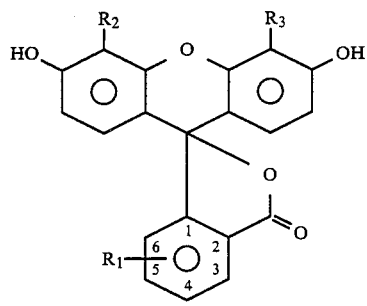

wherein: $R_1$ is attached at the 5- or 6- position and $R_1$ is a pyridoxamide group, or a carboxyl group, or a group of Formula II,

in which

X is carbonyl, aminothiocarbonyl, or methylene,
Y is hydrogen, lower alkyl, carboxy alkyl, or lower alkylol, and
Z is carboxy alkyl, lower alkylol or a monoor di-saccharide group or pyridoxyl; and $R_2$ and $R_3$ are the same or different and may be hydrogen or a group of Formula II. The lower alkyl may be from one to seven carbons long, the lower alkylol may be a one to six carbon alcohol such as ethylol, or tris(methylol) methyl and the carboxy alkyl may be from two to seven carbons long, and the mono- or disaccharide can be for example, galactose, glucose, or maltose residues.

Compounds of Formula I may be provided and used as isomeric mixtures containing both the 5- and 6substituted forms or containing essentially one isomeric form. It is to be understood that the prefix "5(6)-" used to designate the compounds of the invention encompasses isomeric mixtures containing both the 5- and 6-substituted forms and containing essentially one of the isomeric forms.

Presently preferred compounds of Formula I, wherein $R_2$ and $R_3$ are both hydrogen, include: 5(6)-carboxyfluorescein-N-methylglucamide (hereinafter NMG); 5-carboxyfluorescein-N-methylglucamide; 6-carboxyfluorescein-N-methylglucamide; 5(6)-carboxyfluorescein-tris(methylol)methylamide; 5-carboxyfluorescein-diethanolamide; 5(6)-carboxyfluorescein-N-(βhydroxyethyl)-maltosamide; 5(6)-carboxyfluorescein-galactosamide; 5(6)-carboxyfluorescein-pyridoxamide; fluorescein-5(6)-N-(β-hydroxyethyl)maltose-thiourea; and fluorescein-5(6)-tris(methylol)methyl-thiourea.

Presently preferred compounds of Formula I, wherein $R_2$ and $R_3$ are not hydrogen, include: 5(6)-carboxyfluorescein-tris(methylol)methylamide-4',5'bis (methylenediethanolamine); 5(6)-carboxyfluorescein-N-methylglucamide-4',5'-bis(methylenediethanolamine); 5(6)-carboxyfluorescein-N-methylglucamide-4',5'-bis(N-methylglucaminomethyl); 5(6)-carboxyfluorescein-N-methylglucamide-4',5'-bis(methyleneiminodiacetic acid); 5(6)-carboxyfluorescein-4',5'-bis(methylenesarcosine); and 5(6)-carboxyfluorescein-4',5'-bis(methyleneiminodiacetic acid).

Presently most preferred compounds of the invention are 5(6)-carboxyfluorescein-N-methylglucamide and 5(6)-carboxyfluorescein-tris(methylol)methylamide.

Also provided by the invention are aqueous compositions of the compounds of Formula I at self-quenching concentrations, which compositions can be encapsulated within liposomes to provide reagents suitable for use in lytic assays.

Other aspects and advantages of the present invention will be apparent upon consideration of the following detailed description thereof which includes numerous illustrative examples of practice of the invention.

BRIEF DESCRIPTION OF DRAWINGS

FIG. 1 is a plot of the signal/noise versus time, in days, for five fluorophores; and FIG. 2 is a bar graph of the signal/noise obtained for five different fluorophores at 103 days after preparation.

DETAILED DESCRIPTION

The present invention relates to the discovery and synthesis of novel fluorophores which can be encapsulated and maintained within synthetic liposomes without significant leakage over longer periods of time. When encapsulated at high concentrations, on the order of 50–200 mM, depending upon the signal strength required, the fluorophores are self-quenched and, upon liposome lysis, fluorescence is re-established and can be readily measured.

The following examples illustrate practice of the invention. Example 1 relates to the synthesis of the fluorophores. Example 2 relates to the preparation of liposomes and the encapsulation of the fluorophores and Example 3 relates to leakage studies.

The examples which follow are for illustrative purposes and are not intended to limit the scope of the invention.

EXAMPLE 1

Synthesis of Fluorophores

The fluorophores are generally obtained in an isomeric mixture of both the 5- and the 6-isomeric forms owing to the starting materials used to prepare the fluorophores.

The N-hydroxysuccinimide ester of 5(6)-carboxyfluorescein, is used as a starting material for 5(6)-carboxyfluorescein-N-methylglucamide; 5(6)-carboxyfluorescein-tris(methylol)methylamide; 5-carboxyfluorescein-diethanolamide; 5(6)-carboxyfluorescein-N-(β-hydroxyethyl)-maltosamide; 5(6)-carboxyfluorescein-galactosamide; and 5(6)-carboxyfluorescein-pyridoxamide.

5(6)-carboxyfluorescein-N-methylglucamide is used as the starting material for 5(6)-carboxyfluorescein-tris(-methylol)methylamide-4',5'bis(methylene diethanolamine); 5(6)-carboxyfluorescein-N-methylglucamide-4',5'-bis(methylenediethanolamine); 5(6)-carboxyfluorescein-N-methylglucamide-4',5'-bis(N-methylglucaminomethyl); 5(6)-carboxyfluorescein-N-methylglucamide-4',5'-bis(methyleneiminodiacetic acid); and 5(6)-carboxyfluorescein-4',5'-bis(methylene-sarcosine).

5(6)-carboxyfluorescein (Eastman Organic Chemicals; Rochester, N.Y.) is used as the starting material for 5(6)-carboxyfluorescein-4',5'bis(methyleneiminodiacetic acid).

Fluorescein isothiocyanate (Eastman Organic Chemicals; Rochester, N.Y.) is used as the starting material for fluorescein-5(6)-tris(methylol)methylthiourea; and for fluorescein-5(6)-N-(β-hydroxyethyl)-maltose-thiourea.

Synthesis of 5(6)-carboxyfluorescein-N-hydroxysuccinimide ester

5(6)-carboxyfluorescein N-hydroxysuccinimide ester was synthesized as follows. A 250 ml round bottom flask was charged with 11.28 g (0.03 mole) of 5(6)-carboxyfluorescein, 3.45 g (0.03 mole) of N-hydroxysuccinimide, and 6.18 g (0.03 mole) of dicyclohexylcarbodiimide. The contents were dissolved in 80 ml of dry dimethylformamide and stirred for 16 hours under nitrogen gas. At the end of this period no starting material could be observed by thin layer chromatography. The contents of the flask were concentrated down to 25 ml, and an acetone:toluene (1:3) solution was added to redissolve the crude active ester. This material was purified on preparatory HPLC apparatus using silica gel columns, and an eluent of acetic acid:2-propanol:ethyl acetate (2:50:48). The yield obtained was 10.0 g (70%). The desired structure was confirmed by $^1$-NMR (DMSO-$d_6$) which gave the following chemical shifts:

| | |
|---|---|
| $\delta = 10.2$ | (phenolic OH, 2H) |
| $\delta = 8.6$–7.5 | (phthalide ring, 3H) |
| $\delta = 6.8$–6.5 | (xanthene ring, 6H) |
| $\delta = 2.95$ | (succinimide, 4H) |

In addition, mass spectral analysis gave a molecular ion of: $MS(M+H)^+ = 474$. The structure of the product obtained is given below.

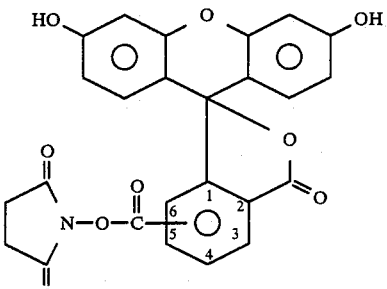

5(6)-carboxyfluorescein N-hydroxysuccinimide ester

Synthesis of 5(6)-carboxyfluorescein-N-methylglucamide

A 1000 ml round-bottom flask was charged with 95 g (0.20 mole) of 5(6)-carboxyfluorescein N-hydroxysuccinimide ester, and 39 g (0.20 mole) of N-methyl-D-glucamine, and 24 g (0.24 mole) of triethylamine. The contents of the flask were dissolved in 750 ml of anhydrous dimethylformamide. After 12 hours of stirring at room temperature under nitrogen gas the reaction was almost complete as shown by thin layer chromatography. The solution was concentrated down to ca. 200 ml and purified by preparatory HPLC using silica gel columns and acetone:acetic acid (50:1) with a gradient of methanol from 2% to 10%. The yield obtained was 47.6 g (43%). The desired structure was confirmed by $^1$H NMR (CD$_3$OD, D$_2$O) which gave the following chemical shifts:

| | |
|---|---|
| $\delta = 8.2$–7.25 | (phthalide ring, 3H) |
| $\delta = 6.8$–6.55 | (xanthene ring, 6H) |

| | |
|---|---|
| δ = 4.3–3.25 | (glucamine, 8H) |
| δ = 3.25–3.05 | (N-methyls, 3H, four peaks; corresponding to syn and anti forms of 5 and 6 carboxyamide groups) |

Mass spectral analysis gave a molecular ion of: MS(M+H)+ = 554.

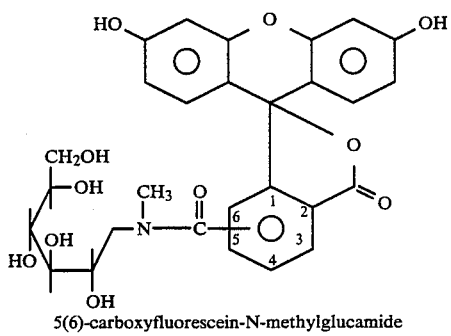

5(6)-carboxyfluorescein-N-methylglucamide

Separation of 5- and 6-Isomers of Carboxyfluorescein-N-methylglucamide

The 5- and 6-isomers of carboxyfluorescein-N-methylglucamide were separated as follows. Crude 5(6)-carboxyfluorescein-N-methylglucamide, 4.2 g (0.0076 moles), was dissolved in 8 ml of 1:1 dimethylformamide and methanol and chromatographed on a 500 ml silica gel column of Waters Associates Pre LC/System 500A HPLC apparatus, using as eluent acetone:methanol:acetic acid (70:2:2) at a flow rate of 0.1 L/min. The fraction which eluted at 3.5 minutes was pure isomer, 5-carboxyfluorescein N-methylglucamide (0.447 g). Later fractions were collected, pooled, concentrated to a volume of 15 ml and allowed to stand overnight at room temperature. Bright yellow crystals precipitated and gave 0.368 g of isomer, 6-carboxyfluorescein-N-methylglucamide. The supernatant was chromatographed again, yielding an additional 1.013 g of isomer, 5-carboxyfluorescein-N-methylglucamide. Thus, 1.460 g of the 5-isomer and 0.368 g of the 6-isomer were obtained.

Synthesis of 5(6)-carboxyfluorescein-tris(methylol)methylamide

A 1000 ml round bottom flask was charged with 63.4 g (0.134 mole) of 5(6)-carboxyfluorescein N-hydroxysuccinimide ester, and 16.2 g (0.134 mole), of tris(hydroxymethyl)aminomethane, and 33.8 g (0.335 mole) of triethylamine. The contents of the flask were dissolved in 200 ml of dry dimethylformamide and stirred under nitrogen for 24 hours. A trace of 4-dimethylaminopyridine was added and the reaction was heated under nitrogen for another hour at 70° C. At the end of this period the reaction appeared complete by thin layer chromatography. The solvent was reduced down to a total volume of 200 ml of a dark red oily solution. This material was purified on preparatory HPLC apparatus using silica gel column and an elution solvent of acetic acid:2-propanol:ethyl acetate (2 8:70). The yield obtained was 20.5 g (32%). The desired structure was confirmed by 1H-NMR (CD3OD) which gave the following chemical shifts:

| | |
|---|---|
| δ = 8.5–7.25 | (phthalide ring, 3H) |
| δ = 6.8–6.5 | (xanthene ring, 6H) |
| δ = 3.9 | (methylenes, 6H) |

Mass spectral analysis gave a molecular ion of: MS(M+H)+ = 480.

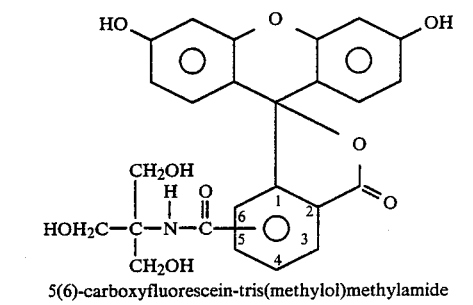

5(6)-carboxyfluorescein-tris(methylol)methylamide

Synthesis of 5(6)-carboxyfluorescein-diethanolamide 948 mg (2 mmol) of 5-carboxyfluorescein N-hydroxysuccinimide ester was dissolved in 3 ml of dimethylformamide and 202 mg of triethylamine were added followed by 234 mg of diethanolamine. The reaction mixture was stirred at 50° C. for 4 hours. This layer chromatography showed formation of a new product and total consumption of 5-carboxyfluorescein N-hydroxysuccinimide ester (silica gel; eluent: methylene chloride, methanol, acetic acid, 73:5:2). The reaction mixture was concentrated in vacuo and crude material purified by column chromatography using 300 g of silica gel and methylene chloride, methanol, acetic acid 73:5:2 as an eluent. The yield obtained was 300 mg.

The structure of 5-carboxyfluorescein-diethanolamide is given below.

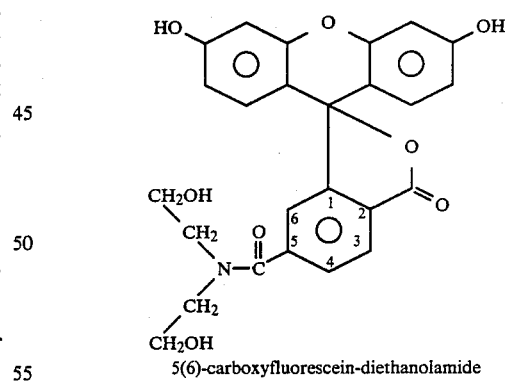

5(6)-carboxyfluorescein-diethanolamide

Synthesis of 5(6)-carboxyfluorescein-N-(β-hydroxyethyl)-maltosamide

5(6)-carboxyfluorescein-N-(β-hydroxyethyl)-maltosamide was synthesized from 0.473 g (0.001 mole) of 5(6)-carboxyfluorescein N-hydroxysuccinimide ester and 0.405 g (0.001 mole) of N-(β-hydroxyethyl)-maltosamine. Work-up and purification were similar to that of 5(6)-carboxyfluorescein-N-methylglucamide, yielding 0.226 g (30%) of product. The structure is shown below.

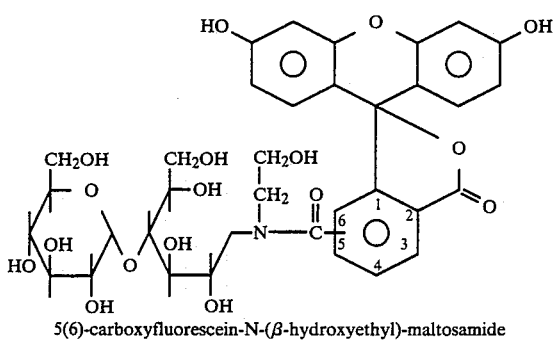

5(6)-carboxyfluorescein-N-(β-hydroxyethyl)-maltosamide

Synthesis of 5(6)-carboxyfluorescein-galactosamide

5(6)-carboxyfluorescein-galactosamide was synthesized from 1.00 g (0.0046 mole) of galactosamine hydrochloride and 2.19 g (0.0046 mole) of (5)6-carboxyfluorescein N-hydroxysuccinimide ester. Work-up and purification were similar to that of 5(6)-carboxyfluorescein-N-methylglucamide, yielding 0.120 g (5%) of product. The structure is shown below.

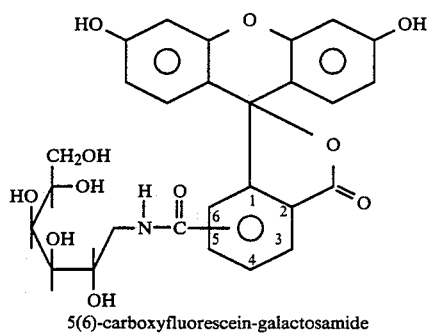

5(6)-carboxyfluorescein-galactosamide

Synthesis of 5(6)-carboxyfluorescein-pyridoxamide

5(6)-carboxyfluorescein-pyridoxamide was synthesized from 1.183 g (0.0025 mole) of 5(6)-carboxyfluorescein N-hydroxysuccinimide ester and 0.603 g (0.0025 mole) of pyridoxamine dihydrochloride in the presence of 1.01 g (0.01 mole) of triethylamine. Work-up and purification were similar to that of 5(6)-carboxyfluorescein-N-methylglucamide, yielding 0.879 g (67%) of product. The structure is shown below.

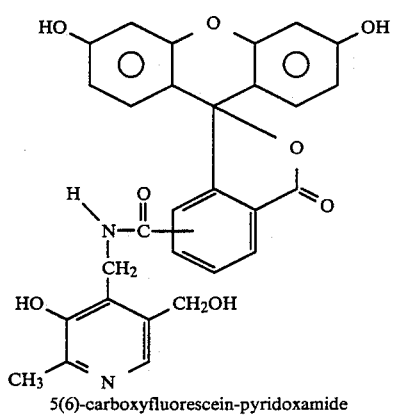

5(6)-carboxyfluorescein-pyridoxamide

Synthesis of 5(6)-carboxyfluorescein-tris(methylol)methylamide-4′,5′-bis(methylenediethanolamine)

A round bottom flask was charged with 0.54 g ($1.1 \times 10^{-3}$ mole) of 5(6)-carboxyfluorescein tris(methylol)methylamide dissolved in 4 ml of acetic acid, and 0.25 g ($2.4 \times 10^{-3}$ mole) of diethanolamine. Slowly, with stirring, 2 ml of 37% aqueous formaldehyde was added and the reaction solution was heated, under reflux, at 80° C. for 4 hours. At the end of that period, 30 ml of toluene were added and acetic acid was removed by azeotropic distillation. The oily residue was washed with acetone and the semi-solid was recrystallized from 6 ml of ethanol-water. Crystals were collected after overnight standing at 4° C., yielding 0.127 g (16% yield) of pure product.

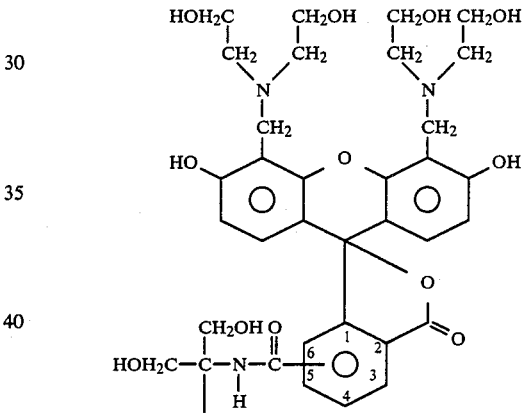

5(6)-carboxyfluorescein-tris(methylol)methylamide-4′,5′-bis(methylenediethanolamine)

Synthesis of 5(6)-carboxyfluorescein-N-methyl glucamide-4′,5′-bis(methylenediethanolamine)

A round bottom flask was charged with 0.50 g ($9.9 \times 10^{-3}$ mole) of 5(6)-carboxyfluorescein-N-methylglucamide, 15 ml of acetic acid, 0.21 g ($2.0 \times 10^{-3}$ mole) diethanolamine, followed by dropwise addition of 37% aqueous formaldehyde. The reaction was stirred under a reflux condenser at 80° C. After 2 hours, the bulk of the acetic acid was evaporated followed by co-evaporation with toluene. The rude reaction product was purified on a XAD-4 chromatography column using water and methanol as eluent. There was obtained 0.55 g (42% yield) of product.

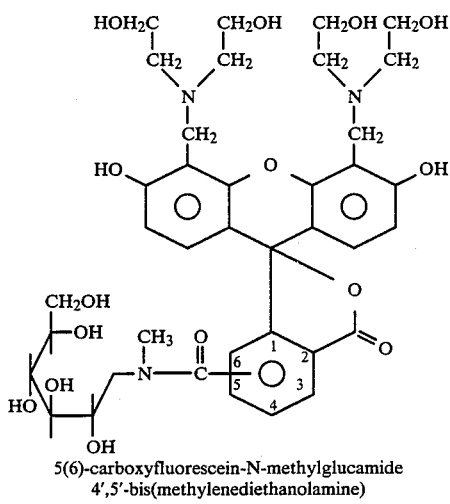

5(6)-carboxyfluorescein-N-methylglucamide
4′,5′-bis(methylenediethanolamine)

Synthesis of 5(6)-carboxyfluorescein-N-methyl glucamide-4′,5′-bis (N-methylglucaminomethyl)

100 mg of 5(6)-carboxyfluorescein-N-methyl glucamide (0.18 mmol), prepared as described above, and 84 mg (0.43 mmol) of N-methyl-D-glucamine were dissolved in 2 ml of glacial acetic acid. 145.9 mg of a 37% solution of formaldehyde was added and the reaction mixture stirred at 65–70° C. for 24 hours. The reaction mixture was concentrated in vacuo to 0.5 ml. The product was crystallized from the solution and was filtered through a Buechner funnel. The yield obtained was 48%.

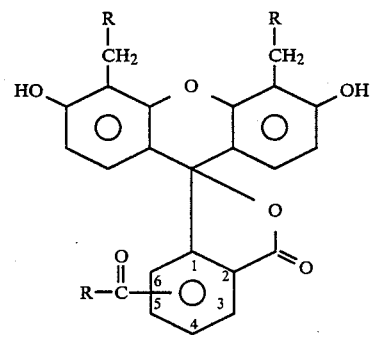

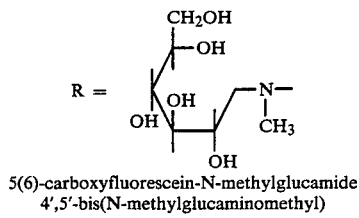

5(6)-carboxyfluorescein-N-methylglucamide
4′,5′-bis(N-methylglucaminomethyl)

Synthesis of 5(6)-carboxyfluorescein-N-methylglucamide-4′,5′-bis(-methylene-iminodiacetic acid)

A three-necked 200 ml flask, equipped with a magnetic stirrer, thermometer and reflux condenser, was charged with 1.50 g ($2.7 \times 10^{-3}$ mole) of 5(6)-carboxyfluorescein-N-methylglucamide dissolved in 15 ml of glacial acetic acid, and 0.76 g ($5.7 \times 10^{-3}$ mole) of iminodiacetic acid. The mixture was stirred and heated at 50° C., and 4.43 g of 37% aqueous formaldehyde was added dropwise. Heating was continued for 1 hour at 65–70° C., and disappearance of starting material was complete after that time period, as confirmed by thin layer chromatography (70:25:2 acetone-methanol-acetic acid). Acetic acid was removed by azeotropic distillation with toluene and the crude produce was recrystallized from a minimal volume of water, yielding 0.28 g (12.3%) of pure product.

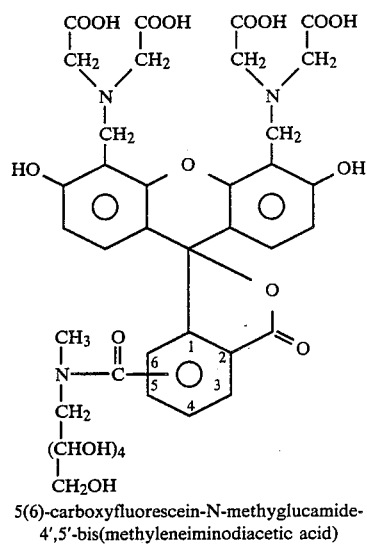

5(6)-carboxyfluorescein-N-methyglucamide-
4′,5′-bis(methyleneiminodiacetic acid)

Synthesis of 5(6)-carboxyfluorescein-4′,5′-bis(methylenesarcosine)

A 100 ml round bottom flask was charged with 3.76 g (0.01 mole) of 5(6)-carboxyfluorescein, 25 ml of 1:2 2-propanol-acetic acid and heated until the 5(6)-carboxyfluorescein dissolved. Then, 1.78 g (0.02 mole) of sarcosine was added followed by 8.11 g of 37% aqueous solution of formaldehyde and the reaction mixture was heated at 80° C. for 75 minutes. After that period, no starting material could be seen by thin layer chromatography. The reaction solution was filtered hot and, on cooling the product crystallized. This material was recrystallized from 1:1 ethanol-water yielding 0.60 g (10% yield) of pure material.

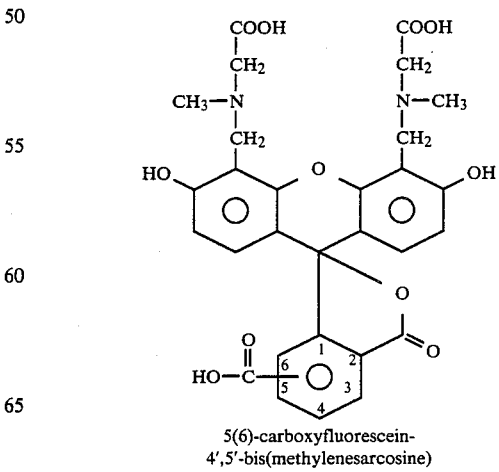

5(6)-carboxyfluorescein-
4′,5′-bis(methylenesarcosine)

Synthesis of 5(6)-carboxyfluorescein-4',5'-bis(methyleneiminodiacetic acid)

553 mg of 5(6)-carboxyfluorescein and 266 mg (2mmol) of iminoacetic acid was placed in a flask and 25 ml of glacial acetic acid-methanol (15:10) added followed by 1.6 g of 37% formaldehyde. The reaction mixture was stirred at 70° C. for 16 hours and then concentrated in vacuo. Crude product was dissolved in 15 ml of 5% sodium hydroxide and purified by column chromatography on Dowex 50X-2-200 ion exchange resin. The yield obtained was 35%. The structure of 5(6)-carboxyfluorescein-4',5'-bis(methyleneiminodiacetic acid) is given below.

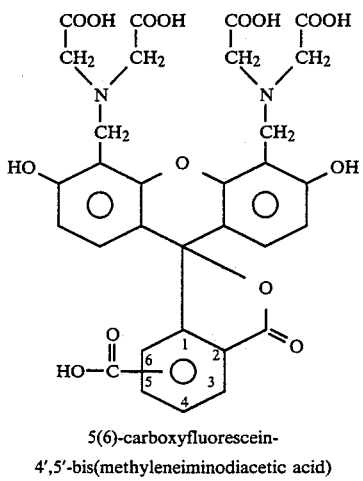

5(6)-carboxyfluorescein-4',5'-bis(methyleneiminodiacetic acid)

Synthesis of fluorescein-5(6)-N-(β-hydroxyethyl)-maltose-thiourea

A 50 ml round-bottom flask was charged with 0.405 g (0.001 mole) of N-(β-hydroxyethyl)-maltosamine, and 0.389 g (0.001 mole) of fluorescein isothiocyanate in 5 ml of anhydrous dimethylformamide. The reaction mixture was stirred under nitrogen for 56 hours. Thin layer chromatography on silica gel, using ethyl acetate:methanol (4:1) showed almost complete conversion of the starting materials to product. After addition of 20 ml of acetone and 25 ml of chloroform a yellow crystalline precipitate formed. The crystals were filtered through a sintered glass funnel and dried for 1 hour at room temperature. The resulting product gave a single spot on thin layer chromatography with an $R_f$ of 0.49 using 2-propanol:acetone:water:acetic acid (50:40:8:2). The yield obtained was 0.546 g (70%). Mass spectral analysis gave a base peak ion of: MS FAB $(M+H)^+ = 777$. The structure of the compound is given below.

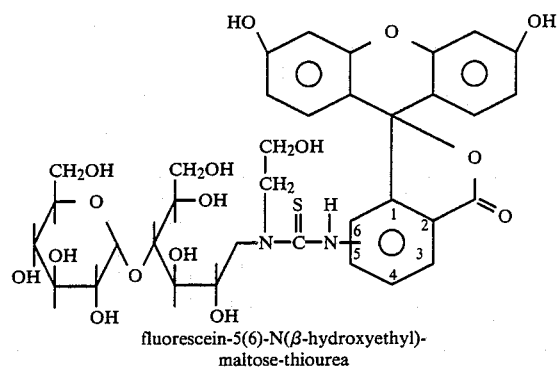

fluorescein-5(6)-N-(β-hydroxyethyl)-maltose-thiourea

Synthesis of fluorescein-5(6)-tris(methylol)methyl-thiourea

Fluorescein 5(6)-tris (methylol)methyl thiourea was synthesized according to the procedures described for the synthesis of fluorescein 5(6)-N-(β-hydroxyethyl)-maltose thiourea except that 0.130 g (0.0003 mole) of fluorescein isothiocyanate and 0.040 g (0.0003 mole) of tris(hydroxymethyl)aminomethane was used yielding 0.120 g (73%) of product.

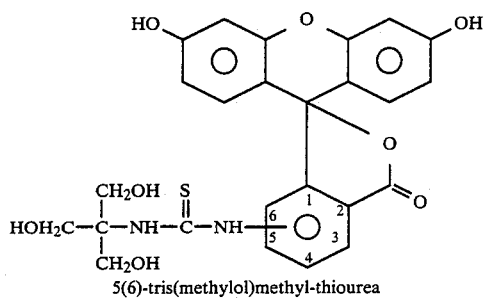

5(6)-tris(methylol)methyl-thiourea

EXAMPLE 2

This example relates to the preparation of liposomes, encapsulation of fluorophores, and initial screening of fluorophores for their acceptability.

A. Preparation of Liposomes

Multilamellar vesicles (MLV) containing a fluorophore to be evaluated were prepared as follows. A 1:1 (molar ratio) egg sphingomyelin:cholesterol solution was prepared from 10 mg/ml stock solutions in 9:1 (volume ratio) chloroform:methanol. $^{14}$C-sphingomyelin was added as a tracer for subsequent lipid quantitation. A solution containing 5 μmoles total lipid was evaporated to dryness under vacuum in a 10 ml pear-shaped flask on a rotary evaporator. The lipid was redissolved once by adding 1.0 ml of 9:1 chloroform:methanol. A 10 μl aliquot was removed for lipid scintillation counting. The solution was again evaporated to dryness to leave a thin lipid film on the inside surface of the flask. Residual solvent was removed by overnight lyophilization.

Each fluorophore to be evaluated was dissolved in distilled, deionized water and titrated to pH 7.4 with sodium hydroxide. The concentration of each fluorophore was 100 mM. Generally, a self-quenching concentration of fluorophore varies with the particular fluorophore and ranges from approximately 1 mM to the upper solubility limit of the fluorophore. Osmolalities of the solutions were measured with a freezing point osmometer. A stock buffer solution containing 50 mM HEPES (N-2-hydroxyethylpiperazine-N'-2-ethane sulfonic acid), and 150 mM sodium chloride, titrated to pH 7.4 with sodium hydroxide, was prepared. This stock buffer solution was then diluted with distilled, deionized water to prepare a series of buffers isotonic with each of the fluorophore solutions. One part buffer solution was then added to 9 parts of each corresponding fluorophore solution.

To prepare the liposomes, 450 μl of fluorophore solution was added to the dry lipid film. The film was allowed to hydrate 30 minutes at room temperature. The liposomes formed spontaneously during this time. The lipid dispersion was vortexed for 45 minutes on a tube mixer and then allowed to stand an additional 30 minutes at room temperature. The lipid bilayers were annealed by heating to 45° C. then slowly lowering the temperature, at a rate of 2° C. per hour, to 6° C.

Unencapsulated fluorophore was removed via centrifugation as follows. The liposome preparation was transferred to a 50 ml centrifuge tube. Thirty ml of isotonic buffer was added. The fluorophore-containing liposomes were pelleted by centrifugation for 30 minutes at 39,000×g. The supernatant was removed by aspiration and the liposomes resuspended in 30 ml isotonic buffer. This was repeated a total of four times. The liposomes were resuspended in 30 ml isotonic buffer. A 300 μl aliquot was removed for scintillation counting to quantitate the lipid. Afterwards, the liposomes were diluted to 33 nanomoles/ml with isotonic buffer and stored at 2-8° C.

B. Quantitative Evaluation of Fluorophore Leakage

To determine the relative amount of fluorophore inside the liposomes, the fluorescence was measured before and after detergent lysis. Just prior to measurement, the liposomes were diluted 1:50 with the appropriate isotonic buffer. Fifty μl of this dilute liposome suspension were then added to 950 μl isotonic buffer to give a final lipid concentration of 33 moles/ml. The background fluorescence intensity of the suspension was measured using an excitation wavelength of 490 nm and an emission wavelength of 520 nm. The liposomes were then lysed by adding 50 μl of an 18% (weight/volume) solution of octyl-β-D-glucopyranoside, after which the total fluorescence was measured.

The signal/noise ratio (S/N) was calculated from (total fluorescence - background fluorescence)/background fluorescence. This is a more sensitive measure of leakage than the encapsulation ratio (ER) which is given by $$ER = \frac{\text{Total fluorescence} - \text{Background fluorescence}}{\text{Total Fluorescence}}$$

$$= \frac{S/N}{S/N + 1}$$

Of the many derivatives synthesized and tested for leakage and evaluated for quantum yield, general spectral characteristics, and ease of preparation/purification, Table 1 lists those compounds found to be most suitable for use in a liposome assay. For some of the compounds listed, the fluorescence quantum yield relative to fluorescein, the RQY factor, is also given. The RQY factor was measured under the conditions described above and it is understood by those skilled in the art that variations in excitation and emission wavelengths can be used to maximize the observed RQY factor and to suitably adapt the fluorophore chosen for a particular application.

Preliminary screening of compounds within the scope of the invention, i.e., fluorescein-4',5'-bis(methylenediethanolamine); 5(6)-carboxyfluorescein-pyridoxamide 4',5'-bis(methylenediethanolamine); and 5(6)-carboxyfluorescein-N-methylglucamide-4',5'-bis(methylenesarcosine), showed them to be less suitable for use in liposome assays on the grounds of insufficient fluorescence and/or insufficient latency.

TABLE 1

| COMPOUND | $R_1$ | $R_2=R_3$ | RQY* |
|---|---|---|---|
| 5(6)-carboxyfluorescein-N-methylglucamide | —CO—N(CH₃)—CH₂(CHOH)₄—CH₂OH | —H | 0.93 |
| 5-carboxyfluorescein-N-methylglucamide | —CO—N(CH₃)—CH₂(CHOH)₄—CH₂OH | —H | 0.93 |
| 6-carboxyfluorescein-N-methylglucamide | —CO—N(CH₃)—CH₂(CHOH)₄—CH₂OH | —H | 0.93 |
| 5(6)-carboxyfluorescein-tris(methylol)methylamide | —CO—NH—C(CH₂OH)₃ | —H | 0.83 |
| 5-carboxyfluorescein-diethanolamide | —CO—N(CH₂CH₂OH)₂ | —H | 0.92 |
| 5(6)-carboxyfluorescein-N-(β-hydroxyethyl)-maltosamide | —CO—N(CH₂CH₂OH)—C₁₂H₂₃O₁₀ | —H | ND |
| 5(6)-carboxyfluorescein-galactosamide | —CO—NH—CH₂(CHOH)₄—CH₂OH | —H | ND |
| 5(6)-carboxyfluorescein-pyridoxamide | 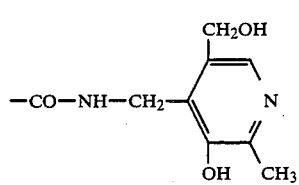 | —H | 0.84 |
| 5(6)-carboxyfluorescein-tris(methylol)methylamide 4',5'-bis(methylene diethanolamine) | —CO—NH—C(CH₂OH)₃ | —CH₂—N(C₂H₄OH)₂ | ND |
| 5(6)-carboxyfluorescein-N-methylglucamide-4',5'- | —CO—N(CH₃)—CH₂—(CHOH)₄—CH₂OH | —CH₂—N(C₂H₄OH)₂ | 0.6 |

TABLE 1-continued

| COMPOUND | R$_1$ | R$_2$=R$_3$ | RQY* |
|---|---|---|---|
| bis(methylenediethanolamine) | | | |
| 5(6)-carboxyfluorescein-N-methylglucamide-4',5'-bis (N-methylglucaminomethyl) | —CO—N(CH$_3$)—CH$_2$(CHOH)$_4$CH$_2$OH | —CH$_2$N(CH$_3$)—CH$_2$(CHOH)$_4$—CH$_2$OH | ND |
| 5(6)-carboxyfluorescein-N-methylglucamide 4',5'-bis (methyleneiminodiacetic acid) | —CO—N(CH$_3$)—CH$_2$—(CHOH)$_4$—CH$_2$OH | —CH$_2$—N(CH$_2$COOH)$_2$ | ND |
| 5(6)-carboxyfluorescein-4',5'-bis(methylene-sarcosine) | —COOH | —CH$_2$N(CH$_3$)—CH$_2$—COOH | 0.44 |
| 5(6)-carboxyfluorescein-4',5'-bis(methyleneimino-diacetic acid) | —COOH | —CH$_2$N(CH$_2$COOH)$_2$ | 0.44 |
| fluorescein-5(6)-N-($\beta$-hydroxyethyl) maltose-thiourea | —NH—CS—N(CH$_2$CH$_2$OH)—C$_{12}$H$_{23}$O$_{10}$ | —H | 0.82 |
| fluorescein-5(6)-tris(methylol) methyl-thiourea | —NH—CS—NH—C(CH$_2$OH)$_3$ | —H | ND |

*RQY — fluorescence quantum yield relative to fluorescein
ND — not determined

EXAMPLE 3

This example relates to a side-by-side comparison of a preferred compound of the invention, NMG, to two commercially available fluorophores.

A. Preparation of Liposomes Used in Side-by-Side Comparison

Multilamellar vesicles of homogeneous size containing the fluorophores to be compared were prepared as follows. A 45:50:5 (molar ratio) solution of sphingomyelin:cholesterol:stearic acid was prepared from stock solutions in 9:1 chloroform:methanol. Sphingomyelin and cholesterol stocks were 10 mg/ml. Stearic acid stock was 5 mg/ml. A solution containing 5 $\mu$moles total lipid was evaporated to dryness under vacuum in a 5 ml pear-shaped flask on a rotary evaporator. The lipid was redissolved once by adding 500 $\mu$l of 9:1 chloroform:methanol. The solution was again evaporated to dryness to leave a thin lipid film on the inside surface of the flask. Residual solvent was removed by overnight lyophilization.

Fluorescein (Eastman Organic Chemicals; Rochester, N.Y.), carboxyfluorescein (Molecular Probes; Junction City, Oreg.) and NMG, prepared according to Example 1, were dissolved in distilled, deionized water and titrated to pH 7.2 with 6N sodium hydroxide (carboxyfluorescein, NMG) or 6 N hydrochloric acid (fluorescein). The concentration of each fluorophore was 100 mM. Five (5) $\mu$l of 1 M HEPES buffer, pH 7.2, were added to 1 ml of each fluorophore. Osmolalities of the solutions were adjusted to approximately 340 mOsm by the addition of sodium chloride.

To prepare the liposomes, 500 $\mu$l of fluorophore solution were heated to 37° C. and added to the dried lipid film. The film was allowed to hydrate 15 minutes at 37° C. The flask containing the fluorophore solution, lipid, was then vortexed for 1 hour at 2300 rpm on a Glas-Col "Big Vortexer", resulting in a suspension of liposomes with an average diameter of 600 nm. The flask contents were heated to 50° C. and the temperature was then slowly lowered, 2° C. per hour, to 4° C. to anneal the liposomes. After 5 days storage at 4° C. the liposome preparation was diluted into 10 ml of isotonic buffer (50 mM HEPES, 150 mM NaCl, 0.02% sodium azide, adjusted to pH 7.2 with sodium hydroxide, osmolality 350 mOsm). The fluorophore containing liposomes were pelleted by centrifugation for 30 minutes at 43,000$\times$g. The supernatant was removed by aspiration and the liposomes resuspended in 10 ml isotonic buffer. This was repeated a total of four times. After the last spin, the liposomes were resuspended in 2 ml isotonic buffer and stored at 2–8° C.

B. Quantitative Leakage Studies

Side-by-side studies were performed comparing two commercially available fluorophores, fluorescein and carboxyfluorescein, to NMG, a representative compound of those derivatives listed in Table 1.

To determine the relative amount of fluorophore inside and outside the liposomes, the fluorescence was measured before and after detergent lysis. Just prior to measurement, the liposomes were diluted 1:500 with isotonic buffer (50 mM HEPES, 150 mM sodium chloride, 0.02% sodium azide, adjusted to pH 7.2 with sodium hydroxide, osmolality:350 mOsm). Fifty $\mu$L of this dilute liposome suspension were then added to 950 $\mu$L isotonic buffer in a glass cuvette. The background fluorescence intensity of the suspension was measured using excitation and emission wavelengths of 490 and 520 nm, respectively. The liposomes were then lysed by adding 50 $\mu$l of an 18% solution of octyl-$\beta$-D-glucopyranoside, after which the total fluorescence was measured. Retention of fluorophore was expressed as signal/noise ratio (S/N), calculated from (total fluorescence-background fluorescence)/background fluorescence.

TABLE 2

SIDE-BY-SIDE LEAKAGE STUDY OF 5(6)-CARBOXYFLUORESCEIN-N-METHYLGLUCAMIDE VS. TWO COMMERCIALLY AVAILABLE FLUOROPHORES

| DAY | FLUORESCEIN | | 5(6)-CARBOXYFLUORESCEIN | | 5(6)-CARBOXYFLUORESCEIN-N-METHYLGLUCAMIDE | |
|---|---|---|---|---|---|---|
| | S/N ($\pm$ s.d.) | PERCENT ENCAPSULATION | S/N ($\pm$ s.d.) | PERCENT ENCAPSULATION | S/N ($\pm$ s.d.) | PERCENT ENCAPSULATION |
| 1 | 25.2 (4.2) | 96.2 | 39.1 (2.5) | 97.5 | 101.5 (4.3) | 99.0 |

TABLE 2-continued

SIDE-BY-SIDE LEAKAGE STUDY OF 5(6)-CARBOXYFLUORESCEIN-N-METHYLGLUCAMIDE
VS. TWO COMMERCIALLY AVAILABLE FLUOROPHORES

| | FLUORESCEIN | | 5(6)-CARBOXYFLUORESCEIN | | 5(6)-CARBOXYFLUORESCEIN-N-METHYLGLUCAMIDE | |
|---|---|---|---|---|---|---|
| DAY | S/N (± s.d.) | PERCENT ENCAPSULATION | S/N (± s.d.) | PERCENT ENCAPSULATION | S/N (± s.d.) | PERCENT ENCAPSULATION |
| 2 | 16.7 (1.1) | 94.3 | 37.9 (0.7) | 97.4 | 90.0 (3.6) | 98.9 |
| 8 | 7.2 (0.1) | 87.8 | 34.3 (0.4) | 97.2 | 75.4 (0.6) | 98.7 |
| 13 | 4.9 (0.2) | 83.0 | 32.4 (0.5) | 97.0 | 70.0 (1.0) | 98.6 |
| 15 | 4.6 (0.1) | 82.1 | 30.8 (0.3) | 96.9 | 64.8 (0.7) | 98.5 |
| 20 | 3.6 (0.2) | 78.3 | 29.8 (0.6) | 96.8 | 63.3 (2.3) | 98.4 |
| 30 | 2.7 (0.1) | 73.0 | 28.3 (0.6) | 96.6 | 57.4 (1.0) | 98.3 |
| 42 | 2.0 (.05) | 66.1 | 26.9 (1.0) | 96.4 | 51.7 (2.0) | 98.1 |
| 62 | 1.4 (0.1) | 58.3 | 25.8 (0.5) | 96.3 | 50.4 (0.6) | 98.0 |
| 90 | 0.96 (.03) | 49.0 | 23.7 (0.03) | 96.0 | 44.7 (1.6) | 97.8 |
| 121 | 0.70 (.03) | 41.2 | 23.3 (0.80) | 95.9 | 41.6 (0.3) | 97.7 |

Table 2 shows that NMG was initially 99.0% encapsulated, i.e., 1% of the marker was external to the liposome and after twenty days 98.4% remained encapsulated within the liposome. In contrast, fluorescein leaked so rapidly from the liposome that, at the initial measurement, only 96.2% was encapsulated. After twenty days, 21.7% of the marker had leaked from the liposome. 5(6)-carboxyfluorescein was initially encapsulated at 97.5%. After twenty days, the encapsulation was 96.8%. Expressed as percent encapsulation, this appears to be only a small amount of leakage. However, the S/N ratio is, after only one day, less than half the S/N ratio of NMG.

FIGS. 1 and 2 show a side-by-side comparison of the time-dependent leakage of calcein and four candidate compounds under the conditions described in Example 2B. 5(6)-carboxyfluorescein-diethanolamide and 5(6)-carboxyfluorescein-tris(methylol)methylamide markers remained 95% encapsulated after 103 days and the two isomers of NMG remained over 96% encapsulated. The encapsulation ratio for calcein was 96.8%. Thus, the six candidate compounds displayed a level of encapsulation nearly equal to that of calcein but without the quenching problems associated with calcein.

The foregoing illustrative examples relate to novel fluorophores which can be encapsulated and maintained within synthetic liposomes without significant leakage over longer periods of time. When encapsulated at high concentrations, the fluorophores are self-quenched and, upon liposome lysis, fluorescence is re-established and can be readily measured. It will be understood that a variety of techniques may alternatively be applied to provide various compounds with properties which can be used in a similar manner. In addition, it will be understood that various modifications of the procedures presented can be adopted.

While the present invention has been described in terms of specific compounds, methods, and compositions, it is understood that variations and modifications will occur to those skilled in the art upon consideration of the present invention. For example, it is envisioned that various fluorescent compounds will be effective as fluorophores according to the present invention. Although the preferred compounds are 5(6)-carboxyfluorescein-N-methylglucamide and 5(6)-carboxyfluorescein-tris(methylol)methylamide it is not intended to preclude other not specifically mentioned or any other effective compounds from being included within the scope of the present invention.

Also, inasmuch as liposomes other than those specifically described have been successfully used, and are, therefore, likely to be similarly effective, it is intended that these other liposome preparations and the like be included within the scope of the present invention.

Numerous modifications and variations of the invention described in the above illustrative examples are expected to occur to those skilled in the art and consequently only such limitations as appear in the appended claims should be placed thereon.

Accordingly, it is intended in the appended claims to cover all such equivalent variations which come within the scope of the invention as claimed.

What is claimed:

1. A lipid vesicle entrapping at a self-quenching concentration a fluorescent compound of Formula I:

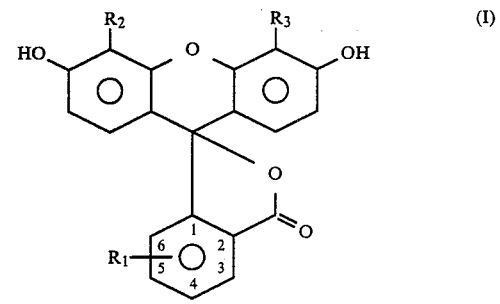

wherein $R_1$ is attached at the 5- or 6- position and $R_1$ is a pyridoxamide group or a carboxyl group or a group of Formula II and $R_2$ and $R_3$ are equivalent or different and are hydrogen or of Formula II:

wherein

X is carbonyl, or aminothiocarbonyl or methylene and

Y is hydrogen, lower alkyl, carboxy alkyl, or lower alkylol, and

Z is carboxy alkyl, lower alkylol or a monoor di-saccharide group or pyridoxyl.

* * * * *